(12) United States Patent
Donnay

(10) Patent No.: US 10,386,357 B2
(45) Date of Patent: Aug. 20, 2019

(54) INTERPRETATION OF GAS LEVELS MEASURED VIA BREATH, BLOOD AND SKIN AFTER DIFFERENT BREATH-HOLDING TIMES

(71) Applicant: Albert Donnay, Hyattsville, MD (US)

(72) Inventor: Albert Donnay, Hyattsville, MD (US)

(*) Notice: Subject to any disclaimer, the term of this patent is extended or adjusted under 35 U.S.C. 154(b) by 764 days.

(21) Appl. No.: 14/900,161

(22) PCT Filed: Jun. 30, 2014

(86) PCT No.: PCT/US2014/044876
§ 371 (c)(1),
(2) Date: Dec. 20, 2015

(87) PCT Pub. No.: WO2015/002880
PCT Pub. Date: Jan. 8, 2015

(65) Prior Publication Data
US 2016/0153964 A1  Jun. 2, 2016

Related U.S. Application Data

(60) Provisional application No. 61/841,737, filed on Jul. 1, 2013.

(51) Int. Cl.
*A61B 5/1455* (2006.01)
*G01N 33/49* (2006.01)
*A61B 5/083* (2006.01)
*A61B 5/00* (2006.01)

(52) U.S. Cl.
CPC ....... *G01N 33/4925* (2013.01); *A61B 5/0833* (2013.01); *A61B 5/0836* (2013.01); *A61B 5/14551* (2013.01); *A61B 5/6816* (2013.01); *A61B 5/6826* (2013.01); *A61B 5/7278* (2013.01)

(58) Field of Classification Search
None
See application file for complete search history.

(56) References Cited

U.S. PATENT DOCUMENTS

| | | | |
|---|---|---|---|
| 5,293,875 A | * | 3/1994 | Stone .................. G01N 33/497 128/204.22 |
| 8,417,305 B2 | | 4/2013 | Dixon |
| 2007/0149891 A1 | | 6/2007 | George et al. |

OTHER PUBLICATIONS

Jan. 5, 2015, International Preliminary Report on Patentability issued in application PCT/US14/44876.
Jan. 5, 2015, Written Opinion of International Search Authority issued in application PCT/US14/44876.
Jan. 1, 1996, Sasse S, Berry R, Nguyen T: Arterial blood gas changes during breath-holding from functional residual capacity. Chest 110,958, 1996.

* cited by examiner

*Primary Examiner* — Eric F Winakur
*Assistant Examiner* — Marjan Fardanesh
(74) *Attorney, Agent, or Firm* — Neifeld IP Law, PC

(57) ABSTRACT

A method or device for assaying physiological gas levels in a human, comprising: repeatedly measuring a gas in samples of breath or blood, or continuously measuring the gas through the skin or fingernail, while he or she holds his or her breath for a specified time interval (BHt) before each measurement, wherein these time intervals are selected from the group consisting of BHt=0, 4-6, 20-25 and 35-40 seconds, and recording the results to form a series of values including at least one measurement at BHt=35-40 which is treated as representing the average gas level in all the tissues of the body (T) at that time, to determine if the individual is net inhaling, net exhaling or in equilibrium with the gas.

2 Claims, No Drawings

INTERPRETATION OF GAS LEVELS MEASURED VIA BREATH, BLOOD AND SKIN AFTER DIFFERENT BREATH-HOLDING TIMES

CROSS REFERENCE TO RELATED APPLICATIONS

This application is the US national stage entry of PCT/US2014/044876, filed Jun. 30, 2014, which claims the benefit of U.S. Provisional Application No. 61/841,737, filed Jul. 1, 2013; and these applications are both incorporated herein by reference.

FIELD

Methods for interpreting the levels of gases measured with breath, blood and transcutaneous gas analyzers after different breath holding times

BACKGROUND

Depending on the gas, measurements made after different breath holding times represent different physiological parameters that change as blood circulates through lungs, arteries, tissues and veins. The clinical utility of existing and future gas measurement devices could be greatly extended by configuring firmware and/or software to record, track and calculate the values in gas measurements made after various breath holding times. The present breath holding methods do not require modifying existing devices, however, beyond selecting the shortest available averaging mode, and can by used anyone simply by holding his or her breath as specified and performing the specified measurements and calculations.

Breath holding time zero [BHt=0] always measures the compartment being sampled. If testing breath, BHt=0 represents the gas level in the lung, if testing blood, BHt=0 represents gas level in the arterial or venous blood at the site drawn, and if testing via skin, BHt=0 represents gas level in whatever organ or tissue type the transcutaneous sensor is placed over, such as an earlobe or fingertip. But beyond BHt=0, the meaning of such measurements is not so clear.

The present invention provides a general method for measuring the relative concentrations of gases that diffuse readily across biological membranes in humans such as carbon monoxide (CO), nitric oxide (NO), hydrogen ($H_2$), and hydrogen sulfide ($H_2S$). The method compares relative levels of the gas from the lungs (L), arteries (A), veins (V) and the average of all tissues (T) by having the subject hold his or her breath for a series of specified times while making repeated or continuous measurements from the same site.

For CO, NO, $H_2$, $H_2S$ and other light gases produced endogenously throughout the body in lungs, blood vessels, and/or tissues that also may be inhaled from exogenous sources, breath holding allows the different levels of these gases normally present in different parts of the body to equilibrate within about 35-40 seconds as the blood continues circulating. This is defined as the average of all tissues, T. Shorter breathholding times estimate the levels of gases originally in the lungs (L), arteries (A), and veins (V) when breathholding began.

The differences between the L, A, V and T measures indicate whether a subject is net absorbing the gas (as during current or recent exogenous poisoning), net excreting the gas (as occurs during endogenous poisoning and/or after exogenous poisoning), or within the range of healthy human dynamic equilibrium. Measurements made at breath holding times [BHt] of 0, 4-6, and 20-25 seconds may be the same or different from those made at 35-40 seconds, which estimates the average level in all tissues after they have reached equilibrium with the circulating blood, when T=L=A=V.

In one embodiment of the invention measuring CO via breath, the calculated differences L minus T (L-T or $\Delta$LT) and A minus V (A-V or $\Delta$AV) are used to determine whether the gas is being net inhaled or net exhaled. In another embodiment measuring CO via blood, the calculated differences used to determine net inhalation or exhalation are A-T and T-V, but only one is needed so less painful venous blood samples are recommended.

For all gases measured in breath, at BHt=0 the sample exhaled during the first 2 seconds of a sustained exhalation originates from the mouth and trachea. During the last 2 seconds of exhalation the sample originates from the deepest lung, where most alveoli are and where most gases exchange with blood. This is defined as an end-tidal (ET) sample. These principles have been recognized in pulmonary physiology for centuries. Most FDA-approved breath analyzers specify the measurement of ET samples, while a few specify mouth samples (e.g., measuring $H_2S$ in the mouth as an index of halitosis).

What is expected to happen to exhaled gas levels at BHt values greater than zero depends on which gas is being measured, how deeply the subject inhaled before starting breath holding, whether this inhalation was via nose, mouth, or both, and whether the exhalation was via the nose or mouth, and whether the subject was supine (which yields highest ET concentrations]) seated or standing (which yields lowest ET concentrations).

In the present method the subject preferably inhales deeply via the nose before starting to hold his or her breath, as opposed to starting to hold the breath after an exhalation (which is both difficult to do and difficult to replicate), and then exhales via the mouth. The present method requires that a subject consistently either lie flat or sit up with their back as straight as possible during gas sampling.

For primarily inhaled gases such as oxygen ($O_2$) that are always net consumed in tissues, the direction of the overall flow is already known (into the body), but there is still a need to estimate the rate of oxygen transfer from blood into tissues. This is accomplished by measuring the oxygen level at any site by any means at two different BHt and subtracting the difference. The present method recommends BHt=20 and 35 for this purpose since earlier times cannot be used for oxygen because the measured level rises briefly for a few seconds as a result of the immediately preceding deep inhalation and may take up to 10 seconds to reach a short-lived maximum before reversing and gradually declining. This anomaly is not seen if breath holding begins after an exhalation.

For primarily exhaled gases such as carbon dioxide ($CO_2$) that are always net produced in tissues, the direction of overall flow is likewise known (out of the body), and there is a similar need to estimate the rate of carbon dioxide transfer from tissues into blood. As with oxygen, this is accomplished by measuring carbon dioxide level at any site by any means at two different BHt and subtracting the difference. The present method recommends BHt=20 and 35 for this purpose. Earlier times cannot be used for carbon dioxide because the measured level falls briefly for a few seconds as a result of the immediately preceding deep inhalation and may take up to 10 seconds to reach a short-lived minimum before reversing and gradually rising. This anomaly is not seen if breath holding begins after an exhalation.

The differences seen in oxygen and carbon dioxide after breath holding of various times are already recognized as important clinical indexes of lung function, oxygen consumption, and oxidative metabolism, but this is not true of other breath gases such as carbon monoxide, hydrogen sulfide and nitric oxide, for which clinical devices specify only one breath holding time prior to exhalation.

For light gases such as CO, NO, $H_2$, and $H_2S$ that circulate in blood and are both produced and consumed in various tissues, and which may be net inhaled or net exhaled depending on the already-circulating level versus the inhaled concentrations, it is impossible to predict whether levels measured at longer breath holding times will rise or fall consistently or remain constant, as they do if already in equilibrium.

The invention is further described using the example of CO but the same principles apply to other gases for which suitable measuring devices are available. Such gases include $O_2$, $CO_2$, NO, $NO_2$, $SO_2$, $O_3$, $H_2$, $H_2S$ and ethanol.

Many published studies have looked at the effect of different breath holding times (BHt) on measurements of exhaled CO in parts per million (ppm) with the objective of determining the time required to most closely correlate ET breath levels with venous % COHb. The optimum breath holding time was found to be BHt=20-25 seconds after an initial deep inhalation.

Breath holding also can be done after exhalation but this technique is very difficult to do and replicate so it is not recommended. Breath holding may be done:
 a) immediately before discrete gas sampling (e.g. before a blood sample is drawn); or
 b) during continuous sampling (e.g. while oximeter is clipped to finger).

The following publications are representative.

"Effects of acute hypoventilation and hyperventilation on exhaled carbon monoxide measurement in healthy volunteers." Cavaliere F, Volpe C, Gargaruti R, Poscia A, Di Donato M, Grieco G, Moscato U., BMC Pulm Med. 2009 December 23;9:51. doi: 10.1186/1471-2466-9-51.

"Exhaled carbon monoxide is not flow dependent in children with cystic fibrosis and asthma." Beck-Ripp J, Latzin P, Griese M., Eur J Med Res. 2004 November 29; 9(11):518-22.

"Validation of the Natus CO-Stat End Tidal Breath Analyzer in children and adults." Vreman H J, Wong R J, Harmatz P, Fanaroff A A, Berman B, Stevenson D K., J Clin Monit Comput. 1999 December; 15(7-8):421-7

"Evaluation of a fully automated end-tidal carbon monoxide instrument for breath analysis." Vreman H J, Baxter L M, Stone R T, Stevenson D K., Clin Chem. 1996 January; 42(1):50-6.

"Reproducibility of measurements of trace gas concentrations in expired air." Strocchi A, Ellis C, Levitt M D., Gastroenterology. 1991 July; 101(1):175-9.

"Acute effect of smoking on rebreathing carbon monoxide, breath-hold carbon monoxide and alveolar oxygen." Kirkham A J, Guyatt A R, Cumming G., Clin Sci (Lond). 1988 October; 75(4):371-3.

"Is alveolar carbon monoxide an unreliable index of carboxyhaemoglobin changes during smoking in man?" Guyatt A R, Kirkham A J, Mariner D C, Cumming G., Clin Sci (Lond). 1988 January; 74(1):29-36.

"Alveolar carbon monoxide: a comparison of methods of measurement and a study of the effect of change in body posture." Kirkham A J, Guyatt A R, Cumming G., Clin Sci (Lond). 1988 January; 74(1):23-8.

"First versus second portion of expired air and duration of breath holding in the sampling of expired air carbon monoxide." Biglan A, Magis K, Dirocco A, Silverblatt A., Br J Addict. 1986 April; 81(2):283-6.

"The effect of duration of breath-holding on expired air carbon monoxide concentration in cigarette smokers." West R J., Addict Behav. 1984; 9(3):307-9.

"The relationship between alveolar and blood carbon monoxide concentrations during breathholding; simple estimation of COHb saturation." Jones R H, Ellicott M F, Cadigan J B, Gaensler E A., J Lab Clin Med. 1958 April; 51(4):553-64.

"A new method for rapid precise determination of carbon monoxide in blood." Gaensler E A, Cadigan J B Jr, Ellicott M F, Jones R H, Marks A., J Lab Clin Med. 1957 June; 49(6):945-57.

"The absorption of carbon monoxide by the lungs during breath-holding." Forster R E, Fowler W S, Bates D V, Van Lingen N B., J Clin Invest. 1954 August; 33(8):1135-45.

From these studies of CO measured in ET samples exhaled via mouth it is known that:
 1) samples collected at BHt=0 measure the level of CO in the lung at rest;
 2) samples collected at BHt=20-25 seconds correlate most closely with the percent (%) of carboxyhemoglobin (COHb) in venous blood; and
 3) in subjects with recent CO exposure whose internal CO levels have not yet returned to equilibrium, shorter and longer breath holding times give lower CO levels than does a BHt=20-25. The authors interpreted these differences in various ways but never as estimates of either the arterial gas level or the average level in all tissues.

Other studies show that, after hours of continuous exposure to any fixed level of CO, subjects reach dynamic equilibrium as the CO they are inhaling first saturates their lungs, then their arterial blood, then their tissues, and lastly their venous blood up to the same level as in air.

Similarly, in fresh air when the CO level is zero, healthy subjects in equilibrium with this environment will exhale zero CO at all breath holding times from 0 to 40 s. So as BHt extends beyond 25 s the ET CO concentration may stay the same if venous blood and tissues are already in equilibrium. It will fall only if the average level in tissues is now lower than that in venous blood (suggesting a relatively brief period of CO exposure that did not saturate tissues). It will rise only if the level in tissues is still higher due to more CO accumulating in tissues from higher than normal endogenous sources and/or impaired CO metabolism, and/or prior CO poisoning.

Because free CO (that which is unbound to hemoglobin) diffuses readily through capillaries just as free oxygen does, it does not take long for CO to reach this equilibrium point during breath holding. By my own experiments and consistent with results published by others, it takes BHt=35-40 for CO to equilibrate.

Thus I conclude that:
 4) samples collected at or after BHt=35-40 s represent the average equilibrium concentration of all tissues; and
 5) a BHt that best represents arterial CO levels exists and falls between that used to measure lung (BHt=0) and venous blood (BHt=20-25)

Conclusion (4) can be checked by taking both arterial and venous COHb samples at or after BHt=35-40 s. These values should match closely if the average CO level in tissues is really now in equilibrium with both venous and arterial blood.

However during constant exposure to any given CO level it usually takes at least several hours for ET samples to reach equilibrium with inhaled levels. The lower the CO exposure concentration, the longer the time to equilibrium when the level of CO in air>lung>arteries >tissue>veins. Only at and beyond equilibrium are these levels all equal and not changed by any breath holding time.

This fact can be seen easily in healthy people who have no excess CO in their bodies and who, when in equilibrium with fresh air (CO=zero), have the same zero level of CO in their exhaled breath at all breath holding times. However, when put in an exposure chamber with 100 ppm CO, as was commonly done in the 1970 s, they eventually reach equilibrium with the environment so that air=lung=arterial=tissue=venous=100 ppm.

Conclusion (5) proposes that a BHt value exists that represents arterial blood CO levels, and that time value falls between lung (BHt=0) and venous blood (BHt=20-25). The basis for this assertion follows.

First, there is no difference in CO at any BHt for people in equilibrium, so we must consider cases not in equilibrium. During exposure to significant exogenous CO, measurements show the lung CO>average tissue and arterial CO>venous CO, which indicates net absorption of CO from the lungs into the body. After significant exogenous CO poisoning ends and until equilibrium with CO-free air is regained, tissue CO>lung and venous CO>arterial CO. This indicates net excretion of CO from the body.

From the direction of blood flow it seems that any BHt correlating with arterial COHb, if it exists, must fall between the BHt associated with the lung fraction and that associated with the venous fraction. This means in the range of 3 to 17 seconds in non-smokers, given that BHt=0 represents lung CO, and BHt of 20-25 represents venous CO.

In preliminary testing, all subjects were in equilibrium with values of BHt=0 or 1; immediately following a brief CO exposure, subjects showed increases in ET CO at all BHt.

BHt=5 s appears to represent arterial CO levels since this is the time at which a small decrease can be seen which reverses by BHt=10 s and which becomes a steep increase by BHt=15 s, eventually peaking in the BHt=20-25 s venous range.

CO concentration measured around 5 seconds after the start of breath holding was:
a) consistently lower than that measured at BHt=0 if the lung started with a higher level of CO than the arterial blood (into which it diffuses); but
b) consistently higher than that measured at BHt=0 if the lung started with a lower CO level than in arterial blood (into which it could not diffuse).

This is why BHt=5 (+/−1) seconds (about 5 seconds) represents arterial levels better than 10 or 15 seconds.

Values representing lung (L), arteries (A), venous (V) and tissue (T) can be used to calculate the following clinically significant relationships, where T=average equilibrium of CO in all tissues.

$\Delta AV$=net CO in [arteries—veins]
$\Delta LT$=net CO in [lungs—average of all tissues]
$\Delta AT$=net CO in [arteries—average of all tissues]
$\Delta VT$=net CO in [veins—average of all tissues]

All of these gaps may be negative, positive or equal. When all these gaps are positive, the results indicate net CO uptake into tissues; when all negative, net CO excretion from tissues; and when equal, net equilibrium between air, blood and tissues. In the rare cases when some of these gaps are positive and some negative, the subject's CO status is in flux and can only be interpreted on a case-by-case basis after retesting.

SUMMARY OF THE INVENTION

One object of the invention is to provide a method for assaying physiological gas levels, comprising:
a) repeatedly measuring a gas level in a human who has held his or her breath for a specified time interval (BHt) before each measurement, wherein at least two and up to four time intervals are selected from the group consisting of BHt=0, 4-6, 20-25 and 35-40 seconds,
b) recording the results to form a series of values including at least one measurement at BHt=35-40, which is treated as the average gas level in all tissues of the body, including the lungs, arteries and veins,
c) calculating differences between recorded results that represent relative estimates of the level of the gas in lungs minus tissues, arteries minus veins, arteries minus tissues, and/or veins minus tissues,
d) interpreting the recorded and calculated results to determine if the gas is being net inhaled or absorbed versus net exhaled or excreted, and at what relative rate.
4. Another object of the invention is to provide a method for assaying physiological gas levels, comprising:
a) measuring $O_2$ and CO gas levels in a human with a device that continuously measures and displays both the arterial and venous levels of % $O_2Hb$ and % COHb,
b) simultaneously calculating and displaying the difference between the venous and arterial levels of each measure (A-V gaps).

DETAILED DESCRIPTION OF THE INVENTION

Many devices can measure gas levels in humans and are suitable for the present invention. They include transcutaneous monitors, pulse oximeters and pulse CO-oximeters that measure oxygen, carbon dioxide and/or carbon monoxide continuously via non-invasive sensors placed over skin or fingernails. They do not generally specify any breath holding times and assume the user is breathing normally while being monitored.

Devices also exist that measure gases at only one time. These generally do not specify breath holding time, (e.g arterial and venous blood gases, breath alcohol), or require only one specified breath holding time (e.g. 15 s in Bedfont's breath CO analyzers, 20 s in others). They also generally specify only one type of sample (mouth, upper respiratory, or end-tidal) and one route of sampling (via nose or mouth for breath testing, over particular types of tissue such as finger tips, ear lobes, or neonatal heels for TC testing).

Some devices give the option to change the length of an audio-visual BHt countdown but no option for comparing the result of one BHt against another (such as Bedfont's Toxco).

Devices designed to calculate a human's resting or basal metabolic rate specify a breath holding time and display a calculated measure that is based in part on the difference between inhaled and exhaled $CO_2$ and/or $O_2$ at rest. But they do not display the actual level of either gas.

Devices exist that require users to first inhale a gas mixture, hold their breath for a fixed time (e.g. 10 s) and then exhale into the device. The device calculates and displays a result based in part on the difference between the inhaled and exhaled concentrations. The most widely used example is a pulmonary medicine test called the 'Diffusing Capacity of the Lung for Carbon Monoxide.' DLCO was introduced in 1950s and is now widely used by a variety of methods for inhaling CO and then breath holding before exhaling, none of which are hardware or device specific. DLCO devices do not display actual level of CO exhaled or the net difference from inhaled, just a calculated DLCO statistic that also depends on many other variables.

According to the present invention, the above devices may be modified to automatically record and track results, including the clinically important gaps (differences) between values measured at specific breath-holding times, and alert users whenever any of the tracked variables is outside published normal ranges and/or the user's own historical normal ranges for measurements at approximately the same time of day. Gas metabolism varies throughout the day and after meals, so users tracking daily trends should retest themselves at approximately the same time of day and with the same number of hours since their last meal.

EXAMPLES OF THE PRESENT INVENTION

Representative methods of the invention are described below in four parts. The first three parts address the estimate of CO in L, A, V and T via breath, skin and blood measurements, while the fourth addresses how the present method can be extended to the measurement of other gases besides CO.

PART 1—Method for Measuring and Interpreting the Concentration of Gases Exhaled after Different Breath Holding Times: Carbon Monoxide [CO] Via Breath CURRENT STATE OF THE ART: Breath gas analyzers are designed to be used with a single breath hold time (BHt) to estimate either venous or arterial COHb but not both, and not the level of CO in the lungs or the average CO level in all tissues. As such, they cannot determine whether an individual is net inhaling or net excreting CO.

GOAL: To assess CO levels in lungs, arteries, veins and the average of all tissue and whether individual is net inhaling CO, net exhaling CO, or in equilibrium.

METHOD: by varying the breathholding time from 0 to 35-40 seconds, measurements can be made that represent the level of CO in the lungs, arteries, veins and the average of all tissues. For consistency, all measurements must be done while a subject is in the same position, either supine (for highest readings) or seated (lower). Standing is not recommended because some subjects may get dizzy, wobble or faint while holding their breath.

APPLICATION: Method of the invention can be used with any device able to measure CO in intervals of whole ppm or tenths of ppm starting from zero in an ET breath sample. The device or an associated application running on another device must be able to display all measured CO levels and preferably to record and track them over time as well, although a user can do this manually. No changes to the hardware of existing devices are needed, but software and firmware may be adapted to offer users the ability to use the method, calculate the results, display and track them over time.

STEP 1. MEASURE CO IN END-TIDAL BREATH SAMPLES FOUR TIMES: at BHt=0, 5, 20 and 35 seconds in that order. These measurements capture the relative concentrations of CO in Lungs (L), Arteries (A), Veins (V), and average of all Tissues (T), respectively. Results can be recorded and tracked manually by user and/or automatically by device and associated software. If the user cannot hold his or her breath for 35 seconds, the results of the results of the first three tests at BHt=0, 5 and 20—or even any two of these three tests —are enough to evaluate if CO is being abnormally net inhaled or exhaled.

Example 1

Real data collected 1 minute after a single normal inhalation and exhalation by mouth of CO (approximately 500 ppm) with the subject standing: L=84, A=24, V=20, T=19, all in ppm.

STEP 2. CALCULATE GAPS (differences) between CO levels in lungs and tissues, and between arteries and veins. These gaps indicate CO uptake versus CO excretion or when the gaps are both zero, dynamic equilibrium.

They can be calculated manually by the user of the device or calculated by the firmware or software in the device or an associated application. To track results, manual users of the method (or the device automatically) should record the date and time of all measurements LUNG-TISSUE GAP=L-T=$\Delta$LT=CO in Lungs minus CO in Tissues (using Example 1: $\Delta$LT=84−19=+65)

ARTEREO-VENOUS GAP=A-V=$\Delta$AV=CO in Arteries minus CO in Veins (using Example 1: $\Delta$AV=24−20=+4)

Example 2

Re-testing of the subject in Example 1 above 10 minutes after the CO exposure gave L=15, A=15, V=16, T=16.

LUNG-TISSUE GAP=L-T=$\Delta$LT=CO in Lungs minus CO in Tissues (using Example 2: $\Delta$LT=15−16=−1)

ARTEREO-VENOUS GAP=A-V=$\Delta$AV=CO in Arteries minus CO in Veins (using Example 2: $\Delta$AV=15−16=−1)

STEP 3. INTERPRET RESULTS

3A. Regarding the Values of L, A, V and T:

In non-smokers, the typical healthy range of CO is below 7 ppm in L, A, V and T. If the CO level in any one compartment is significantly higher than all the others at any time, the others will either gradually rise to meet it (if the endogenous and/or exogenous CO exposure continues unabated for hours), or if the exposure stops, the highest level will fall quickly along with all the others to some new level of dynamic equilibrium that is lower than all of them.

In smokers, even several hours after smoking L, A, V and T may all contain up to 10-25 ppm CO. During smoking and other acute CO exposures, the lung compartment is the highest and may contain hundreds of ppm above the other compartments In Examples 1 and 2 above, L, A, V and T were all >6 immediately after, as well as 10 minutes after the CO exposure stopped, indicating unhealthy CO levels in all compartments. The lung level started 3 times greater than arterial and 4 times greater than venous. The average of all tissues shows that the CO exposure was not long enough for the body to reach equilibrium with the level of CO being inhaled.

3B. Regarding the Values of the ΔLT and ΔAV Gaps:

In non-smokers and smokers when not smoking, the healthy stable range for ΔLT and ΔAV gaps are each 0-3 ppm. This is due to continuous production of endogenous CO in healthy lungs that enters tissues via arterial blood but which does not all come out via venous blood.

It is considered unhealthy if either or both gaps are >3, which is common in smokers while smoking. A gap indicates disequilibrium with very recent or current exogenous CO poisoning still being absorbed into the body faster than it can be excreted. In Example 1 above, both gaps are greater than 3, with ΔLT=65 and ΔAV=4.

It is also considered unhealthy if either or both gaps are negative (<0). Negative values indicate disequilibrium and unhealthfully high levels of CO coming out of tissues due to prior exogenous and/or endogenous CO exposures that have not yet been fully metabolized to $CO_2$ and/or excreted. In Example 2 above, 10 minutes after exposure both ΔLT and ΔAV gaps were −1.

3C. Regarding the Relative Magnitude of the ΔLT and ΔAV Gaps:

When ΔLT=ΔAV the lung-tissue and arterial-venous gaps are the same size, but the interpretation depends on whether these gaps are zero, positive or negative.

If Δ=0 (both gaps are zero) it indicates a stable equilibrium of CO in the body with CO in air, which is healthy when L, A, V and T are all below 7, but not if they are all much higher.

If Δ>0 (both gaps are positive, as in Example 1) it indicates a net uptake of CO from the lungs into tissues. This may be the result of inhaled exogenous CO and/or higher than normal endogenous production of CO in the lungs. If the CO exposure continues, both gaps will remain positive until equilibrium is reached (at Δ=0), but if CO exposure stops, both gaps will reverse within one hour, cross zero and then remain negative until a new equilibrium is reached.

If Δ<0 (both gaps are negative, as in Example 2) it indicates a net respiratory excretion of CO from tissues which, if breathing CO-free air, should gradually get smaller until a new equilibrium is reached.

When ΔLT and ΔAV are both positive but not equal (as in Example 1) it indicates disequilibrium, with more CO being absorbed from the lungs and arteries into tissues than coming out of the body. Note that such disequilibria usually balance out within a few minutes to hours after CO exposure stops depending on the level and duration of exposures.

When ΔAV and ΔLT are both negative but not equal, it indicates disequilibrium, with more CO being excreted from tissues through veins to lungs than entering tissues from arteries.

Part 2—Method for Measuring and Interpreting the Concentration of Gases Exhaled after Different Breath Holding Times: Example of Co Via Skin or Nails with Pulse Co-oximetry™

CURRENT STATE OF THE ART: Masimo's Rainbow® line of pulse CO-oximeters™ with SET® are designed to be used without any breath holding via a sensor placed over a fingernail, earlobe or heel to measure the percentage of total hemoglobin in arterial blood that is bound to CO in the form of % COHb and to display this as % SpCO® (percent of Hb saturated with CO). The manufacturer does not specify that the measure is arterial, and most independent researchers who have studied the device mistakenly compared the results to venous COHb values on the mistaken assumption that arterial and venous values are always equal or close enough to not make a significant difference. Devices that measure and display % SpCO® can alternately display the functional percent oxygen saturation (% $SpO_2$) by toggling from one screen to another.

GOAL: To assess relative % SpCO® levels in lungs, arteries, veins and the average of all tissues, and whether a subject is net inhaling or net exhaling CO or in dynamic equilibrium, using either the earlobe or fingertip sensor.

METHOD: Measure % SpCO® and % $SpO_2$ with a pulse CO-oximeter™ using either earlobe or fingertip sensor while seated or supine from BHt=0 while breathing normally in and out via the nose and then while holding one's breath for 35 to 40 seconds. As the blood continues circulating during breathholding, the arterial blood measured under the skin sensor at BHt=0 is followed by blood coming from the lungs, then the veins, and finally from the average of all tissues.

The analysis for skin measurements is thus quite different from those breath measurements described above. For consistency, all skin CO measurements should be done while the subject is in the same position, either supine, for highest readings, or seated, and after a consistently large inhalation via the nose. CO measurements made while standing are lowest and not recommended because some subjects may get dizzy, wobble or even faint while breath holding.

APPLICATION: Method of the invention can be used with any device able to measure % SpCO® and % $SpO_2$ continuously via skin sensors on an earlobe or fingertip and display results in intervals of tenths of percent starting from zero. The device or an associated application running on another device must be able to display the measured levels % SpCO® and % $SpO_2$ levels and preferably to record and track them over time as well, although a user can do this manually by toggling back and forth between the screens. No changes to the hardware of existing devices are needed, but software and firmware may be adapted to offer users the ability to use the method, calculate the results, display and track them over time.

STEP 1. MEASURE % SpCO® and % $SpO_2$ levels with an earlobe or fingertip sensor while seated or supine at rest and breathing in and out via the nose without any breath holding (BHt=0). These are both arterial levels. An earlobe sensor is recommended because blood from the lungs reaches the earlobe more quickly than it does the fingertip but either will work. Then start holding the breath and monitor the automatically recorded % SpCO® and % $SpO_2$ levels as the breath holding time increases. Some devices (such as the Masimo Radical-7™) allow users to see both the CO and $O_2$ display on the same screen while others (such as the Masimo Rad-57™ and Rad-87™) require toggling back and forth between two display screens.

STEP 2. PLOT RESULTS manually on paper or view in Masimo software with BHt on x-axis from 0 at least 35-40 seconds and the % SpCO® and % $SpO_2$ levels on the Y-axis (either combined or separate does not matter, but easier to interpret results if combined).

STEP 3. IDENTIFY TIME TO PEAK % $SpO_2$.

The time interval from BHt=0 until the maximum level of % $SpO_2$ is defined as Lt. This is the time it took the richly oxygenated blood that was in the lung at the start of breathholding (after a deep inhalation) to circulate to the site of the skin measurement.

STEP 4. INTERPRET % SpCO® VALUES AT VARIOUS BREATH HOLDING TIMES

4A. The level of % SpCO® in arterial blood (A) is that measured at BHt=0.

4B. The relative % SpCO® level in the lungs (L) is measured at BHt=Lt (from Step 3).

4C. The relative % SpCO® level in the veins (V) is measured at some point between BHt=Lt and BHt=35-40. Although the exact BHt that best estimates the level of % SpCO® in veins cannot be predicted, it occurs approximately 10-15 seconds after Lt.

4D. The relative average of % SpCO® in all tissues (T) is measured at BHt=35-40.

4E. In non-smokers, the typical healthy range of arterial % SpCO® at BHt=0 is below 2%, and the level in the average of all tissues should be the same or lower. If the CO level in any one compartment is significantly higher than all of the others at any time, the others will either gradually rise to meet it (if the endogenous and/or exogenous CO exposure continues unabated for hours), or if the exposure stops, the highest level will fall quickly along with all the others to some new level of dynamic equilibrium that is lower than all of them.

4F. In smokers while they are smoking, A>T with respect to % SpCO®. Thereafter, T>A and both typically remain in the range of 5-10% even hours after smoking. Levels above 5% and 10% in non-smokers and smokers, respectively, are considered acute CO poisoning and should be treated immediately. If chronic, any level over 2% or more in non-smokers is unhealthy.

STEP 5. INTERPRET % SpCO® LINE FROM BHt=0 TO BHt=35-40.

Because the data displayed by pulse CO-oximetry™ devices are continuous, interpretation focuses on the slope of the correlation between BHt and % SpCO from BHt=0 to BHt=35-40 rather than on at any particular times in between. This relationship can be seen at a glance from the shape of the line that connects whatever intermediate values were plotted in Step 2. When the % SpCO® line:

5A. stays flat, it indicates CO is in equilibrium with A=L=V=T without any net inhalation or exhalation.

5B. starts rising and keeps rising, it indicates the CO in A<L<V<T. This is the result of having more CO in tissues than blood or lungs due to prior exogenous CO exposures and/or to increased endogenous production and/or to decreased metabolism of CO in tissues. The upper limit of % COHb associated with endogenous CO-related disorders such as rheumatoid arthritis is approximately 4%, so any level above this indicates continued CO poisoning of tissues from some earlier high level of exogenous CO exposure.

5C. starts falling and keeps falling, it indicates the CO in A>L>V>T. This is the result of a relatively brief but high level of exposure to exogenous CO that recently ended, as might be seen in someone just rescued from inhaling smoke in a fire. The lungs have started to clear but more CO is still in arteries than in either tissues or veins.

5D. starts rising but then reverses and keeps falling, it indicates the CO level originally in either the lungs or veins was higher than that in the arteries, such that L>A>T>V or V>L>A>T. The former could be the result of abnormally high endogenous CO production in the lung, and/or current exogenous CO poisoning, while the latter could be due to similar high endogenous CO in non-lung tissues and/or the balance of CO left in tissues from some prior CO poisoning(s). To determine which is the case, examine the % SpCO® line at time=Lt, when the % SpO$_2$ measure peaks (from Step 3). If the early CO and O$_2$ peaks coincide at BHt=Lt, then the CO peak is clearly from the lung fraction. But if the CO peak occurs more than a few seconds (e.g. 5 seconds) later than the % SpO$_2$ peak arriving from the lung, it must be from the venous fraction that follows.

5E. starts falling but then reverses and rises, it indicates the CO level originally in either the lungs or the veins was lower than that in the arteries, such that A>L<V<T or A>L>V<T. The former could be the result of recent exogenous CO exposure that just ended, with the highest CO level now in tissues, while the latter indicates current CO poisoning. To determine which is the case, examine the % SpCO® line at time=Lt, when the % SpO$_2$ measure peaks (from Step 3). If the early CO minimum and O$_2$ maximum coincide at BHt=Lt, then the low CO level is clearly from the lung fraction and A>L<V. But if the CO minimum occurs more than a few seconds (e.g. 5 seconds) later than the % SpO$_2$ peak arriving from the lung, it must be from the venous fraction that follows and then A>L>V<T PART 3—Method for Measuring and Interpreting the Concentration of Gases Exhaled after Different Breath Holding Times: Example of CO Via Blood CURRENT STATE OF THE ART: Blood samples are taken from an artery or vein but rarely both for determination of the percent carboxyhemoglobin (% COHb) while the patient is seated or supine. No breath holding time is specified, so some people are breathing normally when blood is drawn while others may be holding their breath or hyperventilating due to anxiety about the blood drawing procedure. The blood sample(s) is then analyzed for COHb with a CO-oximeter, gas chromatograph, or other instrument capable of making this measurement with resolution of at least 0.1%. (Each 1% COHb in blood is equivalent to approximately 6 to 7 ppm.) As with % SpCO® measurements, most clinicians and researchers are under the misimpression that arterial and venous % COHb are equal or close enough not to make a clinically significant difference, and so they rarely test both.

GOAL: To assess the % COHb levels in the average of all tissues (T) and either the arteries (A) or the veins (V) and from these two measures, to determine whether an individual is net absorbing CO [from blood into tissues], net excreting CO [from tissues to blood], or in dynamic equilibrium.

METHOD: By taking two blood samples from one skin puncture at BHt=0 and BHt=35-40 seconds, measurements can be made of the level of CO in either the arteries (A) or veins (V), depending which is sampled, and the average of all tissues (T). Blood testing does not allow a meaningful estimate of the lung CO level but this is not needed to interpret the A-T and T-V gaps. Either one of which is sufficient to determine if the individual is net absorbing or excreting CO from his or her tissues. But since even one skin puncture is invasive, painful, and not without risk, embodiments of the invention that require only non-invasive measurements of breath or skin are preferred.

APPLICATION: The method can be used with any device that can measure COHb in a blood sample. No changes to the hardware of existing devices are needed, but software changes may be incorporated to display the results of the four different samples and the gaps between them.

STEP 1. MEASURE COHb from two blood samples drawn from any arterial or venous site (usually elbow or wrist of non-dominant arm; venous is recommended since less painful). The first (air-tight) blood gas sample tube is filled while the subject is breathing normally without holding their breath (BHt=0) and labeled "A" or "V" as the case may be. A second tube is left in while the subject is asked to hold their breath for 35-40 seconds, at which time this now full tube is discarded and replaced with another empty one that is labeled "T".

STEP 2. CALCULATE GAP in % COHb between either arteries and tissues [=A-T=ΔAT] or tissues and veins [=T-V=ΔTV], as appropriate for the blood sample drawn. Gaps can be calculated manually by the user from the measured CO-oximeter results or by firmware or software in the device or an associated application. To track results, manual users of the method (or the device automatically) should record the date and time of all measurements.

STEP 3. INTERPRET RESULTS

3A. Regarding Absolute Values of A, V and T:

In non-smokers, the typical healthy range of % COHb is 0-2% in A, V and T. If the CO level in any one of these compartment is significantly higher than all the others at any time, the others will either gradually rise to meet it (if the endogenous and/or exogenous CO exposure continues unabated for hours), or if the exposure stops, the highest level will fall quickly along with all the others to some new level of dynamic equilibrium that is lower than all of them.

In smokers, even several hours after smoking, each of A, V and T typically are in the range of 5-10% COHb. During smoking and other acute CO exposures, the % COHb in A is higher than in T and V (A>T>V), but post-poisoning this is reversed, with T>V>A.

Levels of A, V and/or T above 10% in smokers and 5% in non-smokers are considered acute CO poisoning and should be treated immediately. If chronic, any level over 2% or more in non-smokers is unhealthy.

When A=T or V=T, this indicates the subject is in equilibrium with CO.

3B. Regarding the Absolute Values of the ΔAT and ΔTV Gaps:

In non-smokers and smokers when not smoking, the healthy stable range for both ΔAT and ΔTV is positive from zero to +1. This is due to continuous production of endogenous CO in healthy lungs that enters tissues via arterial blood but does not all come out via venous blood as some is bound to heme proteins in tissues and some is metabolized to carbon dioxide.

It is considered unhealthy if either gap is >1.

When 66 AT>1%, this disequilibrium indicates very recent or current exogenous CO exposure that is still being absorbed into tissues from A faster than it can be excreted from T.

When ΔTV is >1%, this disequilibrium indicates an unhealthy high level of CO coming out of tissues due to prior exogenous and/or endogenous CO exposures that have not yet been fully metabolized to $CO_2$ and/or excreted.

3C. Regarding the Relative Magnitude of the ΔAT and ΔTV Gaps:

While clinically useful information can be obtained by comparing the size of the AT and TV gaps, to do so requires both arterial and venous punctures, which this method seeks to avoid in order to reduce pain, risk and expense. That said, the method can be validated by drawing both arterial and venous samples at BHt=0 and BHt=35-40 and showing that the results for T are the same. Thus one need only compare the % COHb in A and V. When A=V, the subject is in dynamic equilibrium but they are net inhaling CO when A>V and net exhaling CO when V>A.

PART 4—Applications of Method Apart from Carbon Monoxide Testing.

The method described in parts 1, 2 and 3, to measure the relative levels of CO in L, A, V and T via breath, skin or fingernails, and blood can be adapted straightforwardly to measure the levels of other biologically active and medically significant gases for which suitable instruments exist.

The method could be used, for example, with instruments that measure $O_2$, $CO_2$, and alcohol via breath, blood and skin or nails, and with exhaled breath analyzers that already exist for $H_2$, $H_2S$ and NO. These devices generally measure only one gas in only one compartment (such as artery or vein, lung or tissue) and only after one specified breath holding time interval, if any, usually BHt=0. No changes to the hardware of these devices are required. They need only changes to their firmware and/or software to enable measuring, recording, and displaying values associated with specific breath holding times L, A, V and T.

Even technologically advanced devices that continuously measure both arterial and venous levels of % $O_2Hb$ and % COHb, such as Masimo's line of "pulse CO-oximeters" with signal extraction technology (SET®) only display the arterial results. If they also were to also display the venous values of what Masimo calls SpO2 and SpCO® (which are equivalent to the % $O_2Hb$ and % COHb), the breath holding techniques of the present invention would not be needed to estimate the difference between venous and arterial; and then the devices could also calculate and continuously display the even more clinically significant A-V gaps in $O_2$ and CO. This type of information would also allow users to continuously monitor whether SpCO® was in equilibrium (when A=V), was being net absorbed from arterial blood into tissues (when A-V>0), or was being net excreted (when A-V<0).

Such modified devices could also calculate and display the delivery of oxygen from arterial blood into tissues by the A-V difference or gap in $SpO_2$, which would be far more clinically useful than the arterial saturation level alone, The breath holding methods described in Part 2, above, would still be needed to estimate the relative average % SpCO® level in all tissues, but if the device displayed both A and V results together, users could see how far apart they were at BHt=0 and then watch them converge towards equilibrium during breath holding.

For those gases such as oxygen which are always higher in lungs and arteries than in tissues and veins (or vice versa, like carbon dioxide), comparing measurements made while breathing normally (BHt=0) with those made after some fixed time of breath holding such as from BHt=20 and/or BHt=35 provides a way to compare rates of oxygen uptake and carbon dioxide output per unit time among individuals and even within the same individual if retested later. As above, all measurements should be made either seated or supine for consistency, and they should only start after the initial transient anomalies seen in $O_2$ (going up) and $CO_2$ (going down) associated with the deep inhalation just before breathholding have passed. Hence the recommendation to compare measurements made at BHt=20 and 35.

The invention claimed is:

1. A method for assaying physiological CO levels, comprising:
    a) repeatedly measuring a CO gas level in a human who has held his or her breath for a specified time interval (BHt) before each measurement, wherein at least two and up to four time intervals are selected from the group consisting of BHt=0, 4-6, 20-25 and 35-40 seconds,
    b) recording the results to form a series of values including at least one measurement at BHt=35-40, which is treated as the average gas level in all tissues of the body, including the lungs, arteries and veins, c) calculating differences between recorded results that represent relative estimates of the level of the gas in lungs minus tissues, arteries minus veins, arteries minus tissues, and/or veins minus tissues, d) interpreting the recorded and calculated results to determine if the gas is being net inhaled or absorbed versus net exhaled or excreted, and at what relative rate, wherein CO gas levels are measured in end-tidal (ET) samples of exhaled breath with a CO sensing device, and wherein BHt=0 is measured and treated as representing the level of the gas in the lungs (L), BHt=5 is measured and treated as representing the level of the gas in the arteries (A), BHt=20 is measured and treated as representing the level of the gas in the veins (V) and BHt=35 is measured and treated as representing the average of the gas in all tissues (T), including L, A and V.

2. The method of claim 1, wherein L-T and A-V are calculated and interpreted to determine if CO is being net absorbed or excreted from the human.

* * * * *